US008193152B2

(12) United States Patent
Mossel et al.

(10) Patent No.: US 8,193,152 B2
(45) Date of Patent: Jun. 5, 2012

(54) TREATMENT OR PREVENTION OF HEMORRHAGIC VIRAL INFECTIONS WITH IMMUNOMODULATOR COMPOUNDS

(75) Inventors: Eric C. Mossel, League City, TX (US); Cynthia W. Tuthill, Menlo Park, CA (US); Alfred R. Rudolph, Los Altos Hills, CA (US); Clarence J. Peters, Galveston, TX (US)

(73) Assignees: The Board of Regents of the University of Texas System, Austin, TX (US); SciClone Pharmaceuticals, Inc., Foster City, CA (US)

( * ) Notice: Subject to any disclaimer, the term of this patent is extended or adjusted under 35 U.S.C. 154(b) by 555 days.

(21) Appl. No.: 11/577,645

(22) PCT Filed: Oct. 27, 2005

(86) PCT No.: PCT/US2005/038834

§ 371 (c)(1), (2), (4) Date: Dec. 4, 2008

(87) PCT Pub. No.: WO2006/047702

PCT Pub. Date: May 4, 2006

(65) Prior Publication Data

US 2009/0143313 A1 Jun. 4, 2009

Related U.S. Application Data

(60) Provisional application No. 60/622,022, filed on Oct. 27, 2004.

(51) Int. Cl.
*A61K 38/05* (2006.01)
*A61K 31/405* (2006.01)
*A61P 31/12* (2006.01)

(52) U.S. Cl. .......................................... 514/19; 514/419

(58) Field of Classification Search .................... 514/19, 514/419

See application file for complete search history.

(56) References Cited

U.S. PATENT DOCUMENTS

| | | | | |
|---|---|---|---|---|
| 5,744,452 | A | 4/1998 | Kolobov et al. | |
| 5,916,878 | A * | 6/1999 | Kolobov et al. | 514/19 |

FOREIGN PATENT DOCUMENTS

| | | | |
|---|---|---|---|
| UA | 2006 12948 | | 3/7007 |
| WO | 2005/112639 | A2 | 12/2005 |

OTHER PUBLICATIONS

Snell (Ribavirin—current status of a broad spectrum antiviral agent, Expert Opinion, Pharmacother: 2001, 2(8) pp. 1317-1324).*

Fisher-Hoch (Effective Vaccine for Lassa Fever, Journal of Virology, Aug. 2000, pp. 6777-6783).*

Andrei et al., "Molecular Approaches for the Treatment of Hemorrhagic Fever Virus Infections", XP-000971421, Antiviral Research, (1993), vol. 22, 45-75.

Mairuhu et al. "Treating Viral Hemorrhagic Fever", XP-002473657, IDrugs, 2003 6(11): 1061-1066.

(Continued)

*Primary Examiner* — Brandon Fetterolf
*Assistant Examiner* — Kathrien Cruz
(74) *Attorney, Agent, or Firm* — Cooley LLP

(57) ABSTRACT

An immunomodulatory compound is administered to a patient having, or at risk of a hemorrhagic viral infection.

10 Claims, No Drawings

OTHER PUBLICATIONS

Akinci, E., M. Yilmaz, H. Bodur, P. Onguru, F. N. Bayazit, A. Erbay, and G. Ozet. 2009. Analysis of lymphocyte subgroups in Crimean-Congo hemorrhagic fever. Int.J.Infect.Dis. 13:560-563.

Aronson, J. F., N. K. Herzog, and T. R. Jerrells. 1994. Pathological and virological features of arenavirus disease in guinea pigs. Comparison of two Pichinde virus strains. Am.J.Pathol. 145:228-235.

Bradfute, S. B., D. R. Braun, J. D. Shamblin, J. B. Geisbert, J. Paragas, A. Garrison, L. E. Hensley, and T. W. Geisbert. 2007. Lymphocyte death in a mouse model of Ebola virus infection. J.Infect.Dis. 196 Suppl 2:S296-304.: S296-S304.

Bradfute, S. B., K. L. Warfield, and S. Bavari. 2008. Functional CD8+ T cell responses in lethal Ebola virus infection. J.Immunol. 180:4058-4066.

Burke, D. S. and T. P. Monath. 2001. Flaviviruses, p. 1043-1125. In: D. M. Knipe, P. M. Howley, D. E. Griffin, R. A. Lamb, M. A. Martin, B. Roizman, and S. E. Straus (eds.), Fields' Virology. 4th ed., vol. 1. Lippencott Willliams & Wilkins, Philadelphia, PA.

CDC. 2000. Fatal illnesses associated with a new world arenavirus—California, 1999-2000. MMWR Morb.Mortal.Wkly. Rep. 49:709-711.

Chen, J. P. and T. M. Cosgriff. 2000. Hemorrhagic fever virus-induced changes in hemostasis and vascular biology. Blood Coagul. Fibrinolysis. 11:461-483.

Cosgriff, T. M., P. B. Jahrling, J. P. Chen, L. A. Hodgson, R. M. Lewis, D. E. Green, and J. I. Smith. 1987. Studies of the coagulation system in arenaviral hemorrhagic fever: experimental infection of strain 13 guinea pigs with Pichinde virus. Am.J.Trop.Med.Hyg. 36:416-423.

European Application 05813862 Supplementary European Search Report mailed Apr. 3, 2008.

Fennewald, S. M., J. F. Aronson, L. Zhang, and N. K. Herzog. 2002. Alterations in NF-kappaB and RBP-Jkappa by arenavirus infection of macrophages in vitro and in vivo. J.Virol. 76:1154-1162.

Geisbert, T. W., L. E. Hensley, T. R. Gibb, K. E. Steele, N. K. Jaax, and P. B. Jahrling. 2000. Apoptosis induced in vitro and in vivo during infection by Ebola and Marburg viruses. Lab Invest. 80:171-186.

Gowen, B. B., D. L. Barnard, D. F. Smee, M. H. Wong, A. M. Pace, K. H. Jung, S. G. Winslow, K. W. Bailey, L. M. Blatt, and R. W. Sidwell. 2005. Interferon alfacon-1 protects hamsters from lethal pichinde virus infection. Antimicrob. Agents Chemother. 49:2378-2386.

Guzman, M. G., G. Kouri, L. Valdes, J. Bravo, M. Alvarez, S. Vazques, I. Delgado, and S. B. Halstead. 2000. Epidemiologic studies on Dengue in Santiago de Cuba, 1997. Am.J.Epidemiol. 152:793-799.

Imrie, A., J. Meeks, A. Gurary, M. Sukhbataar, P. Kitsutani, P. Effler, and Z. Zhao. 2007. Differential functional avidity of dengue virus-specific T-cell clones for variant peptides representing heterologous and previously encountered serotypes. J.Virol. 81:10081-10091.

Kalina, W. V., K. L. Warfield, G. G. Olinger, and S. Bavari. 2009. Discovery of common marburgvirus protective epitopes in a BALB/c mouse model. Virol.J. 6:132.:132.

Katz, M. A. and J. F. Starr. 1990. Pichinde virus infection in strain 13 guniea pigs reduces intestinal protein reflection coefficient with compensation. J.Infect.Dis. 162:1304-1308.

Lan, S., S. L. McLay, J. Wang, N. Kumar, H. Ly, and Y. Liang. 2009. Development of infectious clones for virulent and avirulent pichinde viruses: a model virus to study arenavirus-induced hemorrhagic fevers. J.Virol. 83:6357-6362.

Li, G., T. Duan, X. Wu, R. B. Tesh, L. Soong, and S. Y. Xiao. 2008. Yellow Fever Virus Infection in Syrian Golden Hamsters: Relationship between Cytokine Expression and Pathologic Changes. Int.J. Clin.Exp.Pathol. 1:169-179.

Lucia, H. L., D. H. Coppenhaver, and S. Baron. 1989. Arenavirus infection in the guinea pig model: antiviral therapy with recombinant interferon-alpha, the immunomodulator CL246,738 and ribavirin. Antiviral Res. 12:279-292.

Lucia, H. L., D. H. Coppenhaver, R. L. Harrison, and S. Baron. 1990. The effect of an arenavirus infection on liver morphology and function. Am.J.Trop.Med.Hyg. 43:93-98.

Mangada, M. M. and A. L. Rothman. 2005. Altered cytokine responses of dengue-specific CD4+ T cells to heterologous serotypes. J.Immunol. 175:2676-2683.

Monath, T.P. and A. D. Barrett. 2003. Pathogenesis and pathophysiology of yellow fever. Adv.Virus Res. 60:343-95.:343-395.

Mongkolsapaya, J., T. Duangchinda, W. Dejnirattisai, S. Vasanawathana, P. Avirutnan, A. Jairungsri, N. Khemnu, N. Tangthawornchaikul, P. Chotiyarnwong, K. Sae-Jang, M. Koch, Y. Jones, A. McMichael, X. Xu, P. Malasit, and G. Screaton. 2006. T cell responses in dengue hemorrhagic fever: are cross-reactive T cells suboptimal? J.Immunol. 176:3821-3829.

Pavri, K. 1989. Clinical, clinicopathologic, and hematologic features of Kyasanur Forest disease. Rev.Infect.Dis. 11 Suppl 4:S854-9.:S854-S859.

PCT/US05/38834 ISR, IPRP and Wrt Op mailed May 26, 2006.

Peters, C. J. 2002. Human Infection with Arenaviruses in the Americas, p. 65-74. In: M. B. A. Oldstone (ed.), Arenaviruses I-The Eidemiology, Molecular and Cell Biology of Arenaviruses., vol. 262. Springer, Berlin.

Pinheiro, F. P., J. P. Woodall, P. A. Travassos da Rosa, and J. F. Travassos da Rosa. 1977. Studies on arenaviruses in Brazil. Medicina (Buenos Aires) 37:175-181.

Qian, C., P. B. Jahrling, C. J. Peters, and C. T. Liu. 1994. Cardiovascular and pulmonary responses to Pichinde virus infection in strain 13 guinea pigs. Lab Anim Sci. 44:600-607.

Sangkawibha, N., S. Rojanasuphot, S. Ahandrik, S. Viriyapongse, S. Jatanasen, V. Salitul, B. Phanthumachinda, and S. B. Halstead. 1984. Risk factors in dengue shock syndrome: a prospective epidemiologic study in Rayong, Thailand. I. The 1980 outbreak. Am.J.Epidemiol. 120:653-669.

Schaeffer, R. C., Jr., M. S. Bitrick, Jr., B. Connolly, A. B. Jenson, and F. Gong. 1993. Pichinde virus-induced respiratory failure due to obstruction of the small airways: structure and function. Exp.Lung Res. 19:715-729.

Scott, E. P. and J. F. Aronson. 2008. Cytokine patterns in a comparative model of arenavirus haemorrhagic fever in guinea pigs. J.Gen. Virol. 89:2569-2579.

Theiler, M. and C. R. Anderson. 1975. The relative resistance of dengue-immune monkeys to yellow fever virus. Am.J.Trop.Med. Hyg. 24:115-117.

Ukranian application 200705421 Office Action (w/Eng translation) dated Oct. 26, 2009.

Vietnamese application 1-2007-01051 Office Action (w/Eng translation) dated Jun. 3, 2010.

Yauch, L. E., R. M. Zellweger, M. F. Kotturi, A. Qutubuddin, J. Sidney, B. Peters, T. R. Prestwood, A. Sette, and S. Shresta. 2009. A protective role for dengue virus-specific CD8+ T cells. J.Immunol. 182:4865-4873.

Zhang, L., K. A. Marriott, D. G. Harnish, and J. F. Aronson. 2001. Reassortant analysis of guinea pig virulence of pichinde virus variants. Virology. 290:30-38.

Zvilich, M., J. C. Williams, D. Waag, W. R. Rill, R. J. Malli, P. Bell, and M. Kende. 1995. Characterization of the non-specific humoral and cellular antiviral immunity stimulated by the chloroform-methanol residue (CMR) fraction of *Coxiella burnetii*. Antiviral Res. 27:389-404.

Mutchnick, M. G., "Thymosin Treatment of Chronic Hepatitis B: A Placebo-controlled Pilot Trial," Hepatology 14 (3):409-415, 1991.

Translation of an Office Action in the corresponding Ukrainian application dated Jul. 9, 2009.

\* cited by examiner

TREATMENT OR PREVENTION OF HEMORRHAGIC VIRAL INFECTIONS WITH IMMUNOMODULATOR COMPOUNDS

CROSS-REFERENCE TO RELATED APPLICATION

This application claims the benefit of U.S. Provisional Application Ser. No. 60/622,022, filed Oct. 27, 2004, and PCT Application No. PCT/US2005/038834, filed Oct. 27, 2005, both of which are incorporated herein.

BACKGROUND OF THE INVENTION

1. Field of the Invention

The present invention relates to the field of treatment or prevention of hemorrhagic viral infections.

2. Description of the Background Art

Hemorrhagic fever viruses (HFVs) are viruses classified in several taxonomic families. HFVs cause a variety of disease syndromes with similar clinical characteristics, referred to as acute hemorrhagic fever syndromes. The pathophysiologic hallmarks of HFV infection are microvascular damage and increased vascular permeability. HFVs that are RNA viruses include Arenaviridae such as Lassa, as well as South American hemorrhagic fevers including Junin, Machupo, Guanarito, and Sabia viruses, which are the causative agents of Lassa fever and Argentine, Bolivian, Venezuelan, and Brazilian hemorrhagic fevers, respectively, whitewater Arroyo virus and Flexal virus; Filoviridae (Ebola and Marburg viruses); Bunyaviridae: Crimean-Congo hemorrhagic fever virus (CCHFV), Rift Valley fever virus, hemorrhagic fever with renal syndrome-associated hantaviruses, including Hantaan virus, Seoul virus, Dobrava virus (also referred to as Dobrava-Belgrade virus), and Puumala virus, and hantavirus pulmonary syndrome-associated hantaviruses, including Bayou virus, Black Creek Canal virus, New York virus, Sin Nombre virus, Andes virus, Oran virus, Juquitiba virus, Laguna Negra virus, and Lechiguanas virus; and Flaviviridae (dengue, dengue fever, dengue hemorrhagic fever, dengue shock syndrome, Kyasanur Forest disease, Omsk hemorrhagic fever, yellow fever).

Under natural conditions, humans are infected through the bite of an infected arthropod or through contact with infected animal reservoirs. Hemorrhagic fever viruses are highly infectious by aerosol; are associated with high morbidity and, in some cases, high mortality; and are thought to pose a serious risk as biologic weapons.

The exact pathogenesis for HFVs varies according to the etiologic agent. The major target organ is the vascular endothelium. Immunologic and inflammatory mediators are thought to play an important role in the pathogenesis of HFVs. All HFVs can produce thrombocytopenia, and some also cause platelet dysfunction. Infection with Ebola and Marburg viruses, Rift Valley fever virus, and yellow fever virus causes destruction of infected cells. Disseminated intravascular coagulation (DIC) is characteristic of infection with Filoviridae. Ebola and Marburg viruses may cause a hemorrhagic diathesis and tissue necrosis through direct damage to vascular endothelial cells and platelets with impairment of the microcirculation, as well as cytopathic effects on parenchymal cells, with release of immunologic and inflammatory mediators. Arenaviridae, on the other hand, appear to mediate hemorrhage via the stimulation of inflammatory mediators by macro-phages, thrombocytopenia, and the inhibition of platelet aggregation.

The incubation period of HFVs ranges from 2 to 21 days. The clinical presentations of these diseases are nonspecific and variable, making diagnosis difficult. It is noteworthy that not all patients will develop hemorrhagic manifestations. Even a significant proportion of patients with Ebola virus infections may not demonstrate clinical signs of hemorrhage.

Initial symptoms of the acute HFV syndrome may include fever, headache, myalgia, rash, nausea, vomiting, diarrhea, abdominal pain, arthralgias, myalgias, and malaise. Illness caused by Ebola, Marburg, Rift Valley fever virus, yellow fever virus, Omsk hemorrhagic fever virus, and Kyasanur Forest disease virus are characterized by an abrupt onset, whereas Lassa fever and the diseases caused by the Machupo, Junin, Guarinito, and Sabia viruses have a more insidious onset. Initial signs may include fever, tachypnea, relative bradycardia, hypotension (which may progress to circulatory shock), conjunctival injection, pharyngitis, and lymphadenopathy. Encephalitis may occur, with delirium, seizures, cerebellar signs, and coma. Most HFVs cause cutaneous flushing or a macular skin rash, although the rash may be difficult to appreciate in dark-skinned persons and varies according to the causative virus. Hemorrhagic symptoms, when they occur, develop later in the course of illness and include petechiae, purpura, bleeding into mucous membranes and conjunctiva, hematuria, hematemesis, and melena. Hepatic involvement is common, and renal involvement is proportional to cardiovascular compromise.

Laboratory abnormalities include leukopenia (except in some cases of Lassa fever), anemia or hemoconcentration, and elevated liver enzymes; DIC with associated coagulation abnormalities and thrombocytopenia are common. Mortality ranges from less than 1% for Rift Valley fever to 70% to 90% for Ebola and Marburg virus infections The nonspecific and variable clinical presentation of the HFVs presents a considerable diagnostic challenge. Clinical diagnostic criteria based on WHO surveillance standards for acute hemorrhagic fever syndrome include temperature greater than 101 F (38.3 C) of less than 3 weeks' duration; severe illness and no predisposing factors for hemorrhagic manifestations; and at least two of the following hemorrhagic symptoms: hemorrhagic or purple rash, epistaxis, hematemesis, hematuria, hemoptysis, blood in stools, or other hemorrhagic symptom with no established alternative diagnosis. Laboratory techniques for the diagnosis of HFVs include antigen detection, IgM antibody detection, isolation in cell culture, visualization by electron microscopy, immunohistochemical techniques, and reverse transcriptase-polymerase chain reaction.

Current therapy for HFVs is largely supportive, but ribavirin has been used with some benefit, depending on the agent. HFV patients tend to respond poorly to fluid infusions and rapidly develop pulmonary edema.

There remains a need in the art for methods of treatment or prevention of hemorrhagic viral infections.

SUMMARY OF THE INVENTION

In accordance with the present invention, a method of treatment or prevention of a hemorrhagic viral infection in a subject comprises administering to said subject an effective amount of an immunomodulator compound of formula A:

$$R-NH-\underset{\underset{COOH}{|}}{CH}-(CH_2)_n-\underset{\underset{O}{||}}{C}-X$$

In Formula A, n is 1 or 2, R is hydrogen, acyl, alkyl or a peptide fragment, and X is an aromatic or heterocyclic amino acid or a derivative thereof. Preferably, X is L-tryptophan or D-tryptophan.

DETAILED DESCRIPTION OF THE INVENTION

In accordance with one embodiment, the present invention relates to treatment or prevention of hemorrhagic viral infections by administering an immunomodulator compound to a subject.

Preferably the subject is mammalian, most preferably the subject is a human patient.

Administration for prevention can be to persons at high risk because of contact with suspected disease carriers, or in carriers who are asymptomatic.

Immunomodulator compounds in accordance with the present invention, comprise immunomodulators of Formula A:

$$R-NH-\underset{\underset{COOH}{|}}{CH}-(CH_2)_n-\underset{\underset{O}{||}}{C}-X \quad (A)$$

In Formula A, n is 1 or 2, R is hydrogen, acyl, alkyl or a peptide fragment, and X is an aromatic or heterocyclic amino acid or a derivative thereof. Preferably, X is L-tryptophan or D-tryptophan.

Appropriate derivatives of the aromatic or heterocyclic amino acids for "X" are: amides, mono- or di-($C_1$-$C_6$) alkyl substituted amides, arylamides, and ($C_1$-$C_6$) alkyl or aryl esters. Appropriate acyl or alkyl moieties for "R" are: branched or unbranched alkyl groups of 1 to about 6 carbons, acyl groups from 2 to about 10 carbon atoms, and blocking groups such as carbobenzyloxy and t-butyloxycarbonyl. Preferably the carbon of the CH group shown in Formula A has a stereoconfiguration, when n is 2, that is different from the stereoconfiguration of X.

Preferred embodiments utilize compounds such as γ-D-glutamyl-L-tryptophan, γ-L-glutamyl-L-tryptophan, γ-L-glutamyl-$N_{in}$-formyl-L-tryptophan, N-methyl-γ-L-glutamyl-L-tryptophan, N-acetyl-γ-L-glutamyl-L-tryptophan, γ-L-glutamyl-D-tryptophan, β-L-aspartyl-L-tryptophan, and β-D-aspartyl-L-tryptophan. Particularly preferred embodiments utilize γ-D-glutamyl-L-tryptophan, sometimes referred to as SCV-07. These compounds, methods for preparing these compounds, pharmaceutically acceptable salts of these compounds and pharmaceutical formulations thereof are disclosed in U.S. Pat. No. 5,916,878, incorporated herein by reference.

The invention is applicable to prevention and/or treatment of hemorrhagic viral infections, including but not limited to Arenaviridae such as Lassa, as well as South American hemorrhagic fevers including Junin, Machupo, Guanarito, and Sabia viruses, which are the causative agents of Lassa fever and Argentine, Bolivian, Venezuelan, and Brazilian hemorrhagic fevers, respectively, Whitewater Arroyo virus and Flexal virus; Filoviridae (Ebola and Marburg viruses); Bunyaviridae: Crimean-Congo hemorrhagic fever virus (CCHFV), Rift Valley fever virus, hemorrhagic fever with renal syndrome-associated hantaviruses, including Hantaan virus, Seoul virus, Dobrava virus (also referred to as Dobrava-Belgrade virus), and Puumala virus, and hantavirus pulmonary syndrome-associated hantaviruses, including Bayou virus, Black Creek Canal virus, New York virus, Sin Nombre virus, Andes virus, Oran virus, Juquitiba virus, Laguna Negra virus, and Lechiguanas virus; and Flaviviridae (dengue, dengue fever, dengue hemorrhagic fever, dengue shock syndrome, Kyasanur Forest disease, Omsk hemorrhagic fever, yellow fever).

Pichinde virus is used as an established model for Lassa fever.

The Formula A compounds may be administered as dosages in the range of about 0.001-10 mg. Dosages may be administered one or more times per week, preferably on a daily basis, with dosages administered one or more times per day. The dosages may be administered by intramuscular injection, although other forms of injection and infusion may be utilized, and other forms of administration such as oral or nasal inhalation or oral ingestion may be employed.

In preferred embodiments, the compounds of Formula A are administered at a dosage within a range of about 0.01-10 mg, more preferably at a dosage of about 0.1-1 mg.

Dosages may also be measured in micrograms per kilogram subject body weight, with dosages in the range of about 0.01-100 micrograms per kilogram, more preferably within the range of about 0.1-10 micrograms per kilogram, and most preferably at about 1 microgram per kilogram.

Included are biologically active analogs having substituted, deleted, elongated, replaced, or otherwise modified portions which possess bioactivity substantially similar to that of SCV-07, e.g., an SCV-07 derived peptide having sufficient homology with SVC-07 such that it functions in substantially the same way with substantially the same activity as SCV-07.

Administration can be by any suitable method, including orally, by injection, periodic infusion, continuous infusion, and the like.

In some embodiments, the Formula A compound is present in a pharmaceutically acceptable liquid carrier, such as water for injection, saline in physiological concentrations, or similar.

Effective amounts of Formula A compound can be determined by routine dose-titration experiments.

The Formula A compound also can be administered with other immune stimulators or antiviral agents.

Arenaviruses pose an ongoing public health concern both from naturally acquired infections and the potential for use as a biothreat agent. The family Arenaviridae is comprised of enveloped viruses with an ambisense, bi-segmented genome. Its 22 members are divided into 2 serocomplexes. The lymphocytic choriomeningitis-Lassa complex, contains the five known 'Old World' viruses while the Tacaribe complex is made up of 17 'New World' viruses of North and South America. Each virus is associated with a single rodent species or with a couple of closely related rodent species reservoir (the possible exception is Tacaribe, which has only been isolated from two species of bats). This close association with the rodent host limits the geographic range of the virus to that of the reservoir. LCMV, being associated with the ubiquitous *Mus musculus*, is the only arenavirus found worldwide.

Asymptomatically infected rodents come into contact with humans, who become infected through the inhalation of virus in aerosolized excreta. Most arenaviruses have not been associated with human infection and not all arenaviruses known to infect humans cause disease. However, several arenaviruses do cause disease in humans that ranges from mild to very severe. The most important are LCMV, which causes a rarely fatal CNS syndrome, Lassa virus, the etiological agent of Lassa fever, and Junin, Machupo, Guanarito, and Sabia, the causative agents of the South American hemorrhagic fevers.

Lassa fever, like the Lassa virus reservoir, *Mastomys* sp., is endemic to West Africa. The disease is characterized by fever, weakness, malaise, headache and sore throat, with an onset 7-18 days after infection. Other common symptoms include joint and back pain, cough, vomiting, and diarrhea. Unlike the hemorrhagic fevers, there is no associated skin rash, ecchymoses, or petechiae. Case fatality among hospitalized patients is 15-20%, but among all Lassa infections may be as low as 2-3%. Aerosolized person-to-person transmission has not been shown to occur. Contact with the secretions of an infected person is a significant risk factor, however.

Junin, Machupo, Guanarito, and Sabia viruses are the etiological agents of the South American hemorrhagic fevers: Argentine, Bolivian, Venezuelan, and Brazilian hemorrhagic fever, respectively. Though distinct, all have similar presentations that include fever, malaise, and myalgia beginning 1-2 weeks after infection. As disease worsens, additional symptoms develop: gastrointestinal distress, dizziness, headache, photophobia, retroorbital pain, tachycardia, petechiae, and conjunctival injection. Machupo infection appears to have the greatest propensity for person-to-person spread, with nosocomial and intrafamilial spread documented. Unlike the other hemorrhagic fever arenaviruses, but similar to Lassa fever infection, deafness has been observed following Guanarito virus infection. Case fatality rate for the South American hemorrhagic fever viruses is around 20%.

Because of their high mortality, aerosol infectivity, and potential to cause a public health crisis, Lassa, Junin, Machupo, Guanarito, and Sabia have been designated category A pathogens by the Center for Disease Control (CDC). Work with these agents must be done using BSL-4 precautions.

Pichinde virus (PIC) is a nonpathogenic Tacaribe complex virus. PIC virulence in guinea pigs was dramatically increased through serial spleen passage in strain 13 guinea pigs. Infection of guinea pigs with the adapted virus produces a disease quite similar to Lassa fever in monkeys and humans. Features include fever, thrombocytopenia, platelet dysfunction, vascular leakage, respiratory distress, viral replication in most extraneural tissues, and minimal histologic changes in infected tissues. Because Pichinde is not pathogenic to man, this model has been extensively used as a low-containment proxy for the study of both Lassa fever and arenavirus hemorrhagic fever.

The nucleoside analogue Ribavirin is the primary antiviral therapeutic for Lassa fever and is a promising therapy for arenavirus hemorrhagic fever. However, while ribavirin therapy may prevent or relieve acute hemorrhagic fever, its use in arenavirus infection has sometimes led to late neurologic disease. Several immunologic treatment modalities have also been tried in animal models of arenavirus infection and disease without success. In vitro, arenaviruses are 10->1000-fold less sensitive to IFNβ than is vesicular stomatitis virus. This insensitivity is supported by studies in Machupo-infected Rhesus monkeys with the IFN-inducing poly (ICLC). Overall mortality and time to death were not improved with therapy and in some groups viremia was significantly higher with treatment. Lucia et al. examined the use of IFNα, ribavirin, and the immunomodulatory drug C246,783 using the PIC-infected guinea pig model. Among the effects of C246,783 are IFN induction and activation of NK cells and macrophages. No significant improvement in mortality was observed among animals treated with IFNα (up to $1.7 \times 10^5$ U) or with C246,783. An improvement in mortality was observed in this study with ribavirin administration if given daily for 28 days after infection; time to death was prolonged with 14 days of treatment. The relative insensitivity of arenaviruses to the type I IFNs probably contributed significantly to the virtual failure of these studies.

Despite these earlier failures of immunotherapy for the arenaviruses, T-cell stimulation is still an unexplored mode of treatment. A pilot study was therefore designed to examine the effect of the immunomodulatory drug SCV-07 on PIC-infected guinea pigs. SCV-07 is known to enhance the Th1 response to immunological stimuli.

SCV-07

SCV-07, γ-D-glutamyl-L-tryptophan, is a member of a class of immunomodulatory drugs that possess γ-glutamyl or β-aspartyl moieties, which was discovered by Russian scientists and is being examined for efficacy in several indications in the U.S. by SciClone Pharmaceuticals, Inc. SCV-07 possesses a number of immunomodulatory activities in vivo and in vitro. SCV-07 increases Con-A-induced thymocyte and lymphocyte proliferation, increases Con-A-induced interleukin-2 (IL-2) production and IL-2 receptor expression by spleen lymphocytes, and stimulates expression of Thy-1.2 on bone marrow cells. In vivo, SCV-07 has a strong immunostimulatory effect on 5-FU-immune-suppressed animals and in a model of immunization with sheep red blood cells.

The discrete mechanism of SCV-07 action has not been rigorously determined. However, based on the above data, it was suggested that SCV-07 acts via its influence on differentiation of pluripotent stem cells to thymocytes and/or differentiation of thymocytes to T-cells. Further, since SCV-07 administration results in increases of the Th1 cytokines IL-2 and IFNγ, but not in Th2 cytokines, it was proposed that SCV-07 acts through a preferential activation of Th1 cells.

Increasing evidence suggests that CD4+ Th1 cells and associated cytokines, including IL-2 and IFNγ, are important in generating a protective immune response to mycobacterial infection. In studies in a murine tuberculosis model, SCV-07 was shown to significantly decrease lung damage. IFNγ production by Con-A-induced spleen cells from SCV-07-treated animals was higher while IL-4 production was lower than in cells from untreated animals. Phagocytic activity by peritoneal macrophages was markedly increased over untreated, infected controls. These pre-clinical data supported the commencement of clinical trials for the use of SCV-07. A phase II clinical trial performed in Russia found that SCV-07 administration increased the incidence of mycobacteria-negative sputum cultures and had a positive effect on cavity healing and symptoms of tuberculosis without any drug-induced adverse effects. SCV-07's efficacy in human tuberculosis cases supports the hypothesis for its efficacy in other diseases in which Th1 immunity has been shown to be important, including arenaviral disease.

Based on the above, two pilot studies were undertaken to examine the efficacy of SCV-07 in treating PIC-infected guinea pigs.

The invention is further illustrated by the following examples, which are not intended to be limiting.

Example 1

20 male Hartley guinea pigs (400-450 g) were divided into groups of five.
Group 0 received no SCV-07
Group 1 received 1 µg/kg SCV-07 i.p. each of the five days prior to infection Group 2 received 1 µg/kg SCV-07 i.p. once on the same day as infection Group 3 received 1 µg/kg SCV-07 i.p. once on the day following infection Infections: animals were inoculated i.p. with 100 pfu guinea pig-adapted PIC.

Body weight and temperature, and surrogate markers for disease progression were measured at least three times per week. Obviously ill animals were assessed more often. Previous work showed that a 25% weight loss represented a terminally ill animal. However, the University of Texas Medical Branch IACUC required that a 20% weight loss would result in classification as terminal and sacrifice of the animal.

Group 0 animals are pooled from two separate experiments; the one described here with treated groups 1-3, and the one described below with treated groups 4-6.

While there is a trend toward efficacy as shown by decreased mortality in the treated groups, Kaplan-Meier survival analysis by the log-rank statistic method supports the visual notion that none of the survival curves of treated animals is significantly different from the survival curve of the control animals (p=0.66, 0.77. and 0.40 for groups 1, 2, and 3, respectively). Weight gain through 11 days post-infection (dpi) among treated animals was greatest in group 1 (Table 1), but for no group was weight gain different from controls. Neither was the temperature, assessed 11 dpi, different between the treated and control animals (Table 2). Not evident from Tables 1 and 2 is the fact that the single control survivor came from the second control group. This animal dramatically skewed the control group temperature to the downside and weight gain to the upside. Therefore, the results from the initial study were more suggestive of efficacy than they appear in the pooled data.

TABLE 1

Average percent weight gain by PIC-infected guinea pigs 10-11 dpi.

| Group | Mean ± Std Dev | P value* |
|---|---|---|
| 0 | 1.79 ± 13.50 | |
| 1 | 0.59 ± 10.71 | 0.48 |
| 2 | −3.75 ± 12.48 | 0.92 |
| 3 | −1.15 ± 12.26 | 0.65 |
| 4 | −0.35 ± 20.07 | 0.64 |
| 5 | 6.73 ± 19.02 | 0.21 |
| 6 | 5.62 ± 16.78 | 0.23 |

*Student's t-test comparison of treated group to group 0.

TABLE 2

Average temperature (° C.) of PIC-infected guinea pigs 10-11 dpi.

| Group | Mean ± Std Dev | P value* |
|---|---|---|
| 0 | 40.35 ± 0.63 | |
| 1 | 40.40 ± 1.00 | 0.72 |
| 2 | 40.48 ± 0.72 | 0.82 |
| 3 | 40.40 ± 0.69 | 0.68 |
| 4 | 40.03 ± 0.59 | 0.23 |
| 5 | 39.38 ± 0.75 | 0.17 |
| 6 | 40.28 ± 0.63 | 0.46 |

*Student's t-test comparison of treated group to group 0.

Though not significant, the first trial was suggestive enough that a second study was initiated.

Example 2

20 animals were again divided into four groups of five.
Group 0 received no SCV-07
Group 4 received 1 µg/kg SCV-07 i.p. on each of the first five days after infection
Group 5 received 10 µg/kg SCV-07 i.p. on each of the first five days after infection
Group 6 received 100 µg/kg SCV-07 i.p. on each of the first five days after infection Infections: animals were inoculated i.p. with 100 pfu guinea pig-adapted PIC.

Body weight and temperature, and surrogate markers for disease progression were measured as described above.

Mortality was decreased in groups 5 and 6, but only group 5 had a survival curve significantly different from group 0 (p=0.77, 0.03, and 0.27 for groups 4, 5, and 6, respectively). Weight gain through 11 dpi was greater in treated groups 5 and 6 than among controls, but the difference was not significant (Table 1). Body temperature was lower in all three treated groups than in controls, but again, the difference was not significant (Table 2). Serum was collected from animals in both experiments. Analysis of these samples is ongoing, but preliminary results suggest undetectable viremia until ~48 hours before acute illness and death.

These results suggest that SCV-07 administration was therapeutic in PIC-infected guinea pigs, as evidenced by a trend towards decreased mortality in several treatment groups, and with significantly decreased mortality at a dose of 10 ug/kg given i.p. for 5 days post infection.

The invention claimed is:

1. A method of treatment of an Arenaviridae infection in a subject comprising administering to said subject an effective amount of an immunomodulator compound of Formula A $$R-NH-\underset{COOH}{CH}-(CH_2)_n-\underset{O}{\overset{\|}{C}}-X \qquad (A)$$

wherein, n is 1 or 2, R is hydrogen, acyl, alkyl or a peptide fragment, and X is an aromatic or heterocyclic amino acid.

2. The method of claim 1, wherein X is L-tryptophan or D-tryptophan.

3. The method of claim 1 wherein said compound is γ-D-glutamyl-L-tryptophan.

4. The method of claim 1 wherein said compound is administered at a dosage within a range of about 0.1-10 mg.

5. The method of claim 1 wherein said compound is administered at a dosage within a range of about 0.1-1 mg.

6. The method of claim 1 wherein said compound is administered at a dosage within a range of about 0.01-100 micrograms per kilogram subject body weight.

7. The method of claim 1 wherein said compound is administered at a dosage within a range of about 0.1-10 micrograms per kilogram subject body weight.

8. The method of claim 7 wherein said compound is γ-D-glutamyl-L-tryptophan.

9. The method of claim 1 wherein the Arenaviridae infection is selected from Lassa fever virus, Junin virus, Machupo virus, Guanarito virus, Sabia virus, Whitewater Arroyo virus or Flexal virus.

10. The method of claim 1, wherein ribavirin is not being administered to the subject.

* * * * *